(12) United States Patent
Flohr et al.

(10) Patent No.: US 9,589,336 B2
(45) Date of Patent: Mar. 7, 2017

(54) RECONSTRUCTION OF IMAGE DATA BY MEANS OF CONTOUR DATA

(71) Applicant: Siemens Aktiengesellschaft, Munich (DE)

(72) Inventors: Thomas Flohr, Uehlfeld (DE); Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 166 days.

(21) Appl. No.: 14/510,425

(22) Filed: Oct. 9, 2014

(65) Prior Publication Data
US 2015/0103969 A1    Apr. 16, 2015

(30) Foreign Application Priority Data

Oct. 14, 2013  (DE) ........................ 10 2013 220 663

(51) Int. Cl.
*A61B 6/00* (2006.01)
*G06T 5/20* (2006.01)
(Continued)

(52) U.S. Cl.
CPC ............... *G06T 5/20* (2013.01); *A61B 6/032* (2013.01); *A61B 6/5205* (2013.01);
(Continued)

(58) Field of Classification Search
CPC .. G06T 5/20; G06T 5/50; A61B 6/032; A61B 6/5205
(Continued)

(56) References Cited

U.S. PATENT DOCUMENTS

2004/0082870 A1* 4/2004 Rudy ................ A61B 5/04085
600/509
2006/0262894 A1  11/2006 Bernhardt et al.
(Continued)

FOREIGN PATENT DOCUMENTS

CN        1864632 A     11/2006
CN      102783962 A     11/2012
(Continued)

OTHER PUBLICATIONS

Bruder H. et al., Efficient Extended Field of View (eFOV) Reconstruction Techniques for Multi-Slice Helical CT; in: Physics of Medical Imaging, SPIE Medical Imaging, Proceedings 2008, vol. 9, No. 30, pp. E2-E13; ISBN: 081947097X, 9780819470973; 2008; DE; Mar. 18, 2008.

(Continued)

*Primary Examiner* — Courtney Thomas
(74) *Attorney, Agent, or Firm* — Harness, Dickey & Pierce, P.L.C.

(57) ABSTRACT

A method is based on first projection data, recorded during a relative rotational movement between an x-ray source of a CT device and at least one examination object lying partly outside the field of view of the CT device. Contour data of the surface of the examination object is useable to enhance the reconstruction of the incomplete first projection data. The spatial correlation between the first projection data and the contour data is known. The first projection data is expanded by way of the contour data to modified projection data, so that the modified projection data includes information about the contour of the examination object lying outside the field of view of the CT device. In an embodiment of the inventive reconstruction of image data by way of the modified projection data, fewer or no artifacts occur by (Continued)

comparison with reconstruction of image data from just the first image data.

20 Claims, 3 Drawing Sheets

(51) Int. Cl.
    *A61B 6/03*      (2006.01)
    *G06T 5/50*      (2006.01)
    *G06T 11/00*     (2006.01)
(52) U.S. Cl.
    CPC .............. *A61B 6/5211* (2013.01); *G06T 5/50* (2013.01); *G06T 11/006* (2013.01); *A61B 6/4441* (2013.01); *A61B 6/5258* (2013.01); *G06T 2211/432* (2013.01); *G06T 2211/436* (2013.01)
(58) Field of Classification Search
    USPC ........................................................ 378/4–20
    See application file for complete search history.

(56) References Cited

U.S. PATENT DOCUMENTS

| 2009/0122955 | A1 | 5/2009 | Bruder |
| 2011/0188723 | A1 | 8/2011 | Bruder et al. |
| 2012/0294504 | A1 | 11/2012 | Kyriakou |

FOREIGN PATENT DOCUMENTS

| DE | 102005022540 A1 | 11/2006 |
| DE | 102007054079 A1 | 5/2009 |
| DE | 102008038330 A1 | 2/2010 |
| DE | 102010006585 A1 | 8/2011 |
| DE | 102011075904 A1 | 11/2012 |
| JP | 2007-143954 | 6/2007 |

OTHER PUBLICATIONS

M., Ismail et al.; "3D-Guided CT Reconstruction using Time-of-Flight Camera", Proc. of SPIE, vol. 7964, Jan. 3, 2011, p. 796429-1-796429-11; 2011.
Bruder H. et al., "Method for reconstructing two dimensional-cut image from computed tomography three dimensional-projection data for use during examining patient, involves reconstructing two dimensional-cut image based on two dimensional-projection data," Thomson Reuters DWPI, Feb. 2010, 1 page, IPAS-BUS.
German Priority Application DE 102013220863.1 filed on Oct. 14, 2013.
German Office Action for Priority Application DE 102013220663.1 dated May 27, 2014.
Korean Office Action and English translation thereof mailed Nov. 11, 2015.
Notice of Allowance issued May 20, 2016 in Korean Patent Application No. 10-2014-0135843.
Office Action for Chinese Application No. 20141051510.X dated Aug. 8, 2016 and English translation thereof.

* cited by examiner

RECONSTRUCTION OF IMAGE DATA BY MEANS OF CONTOUR DATA

PRIORITY STATEMENT

The present application hereby claims priority under 35 U.S.C. §119 to German patent application number DE 102013220663.1 filed Oct. 14, 2013, the entire contents of which are hereby incorporated herein by reference.

FIELD

At least one embodiment of the invention generally relates to a method and/or an imaging system for reconstruction of image data by means of contour data.

BACKGROUND

Computed tomography (CT) is known as a two-stage imaging method. In this method projection data is recorded by an examination object being irradiated with x-ray radiation and the attenuation of the x-rays on their way from the x-ray source to the x-ray detector being recorded. The attenuation is caused by the irradiated materials along the beam path, so that the attenuation can also be understood as a line integral over the attenuation coefficients of all volume elements (voxels) along the beam path. The recorded projection data is not able to be interpreted directly, i.e. it does not produce an image of the irradiated slice of the examination object. Only in a second step is it possible, using reconstruction methods, to compute back from the projection data to the attenuation coefficients of the individual voxels and thus create a picture of the distribution of the attenuation coefficients. In such cases the projection data can comprise a plurality of individual projections which have been recorded from different projection angles. The recording of a plurality of individual projections from different projection angles is also referred to as a scan.

Image data, which represents a two-dimensional image in the form of a slice of the examination object for example, can be reconstructed on the basis of the projection data created during the scan. For example image data also comprises a plurality of two-dimensional images or a contiguous three-dimensional volume. Problems during the reconstruction of the image data emerge if, during the recording of the projection data described above, the examination object protrudes for at least a few of the projection angles beyond the scanning area of the system consisting of x-ray source and x-ray detector. The scanning area is defined by the relative spatial arrangement of the x-rays generated by the x-ray source and the x-ray detector. Within the scanning area complete projection data can be obtained; outside the scanning area complete projection data cannot be obtained. Thus if the examination object protrudes beyond the scanning area, projection data recorded during the irradiation of the examination object is incomplete, which leads to image artifacts during the reconstruction. In order, despite this, to still make possible an image reconstruction which is as precise as possible, a corresponding expansion of the projection data is required for the incomplete projections before the reconstruction. The scanning area is also referred to as the field of view, and methods for reconstruction of image data from the incomplete projection data are also referred to as methods for reconstruction in the expanded field of view. The term scanning area and field of view are used synonymously below.

A method for reconstruction of image data from incomplete measurement data is known from DE 102010006585 A1. In this method first image data is reconstructed from the measurement data and on the basis of the first image data a delimitation of the examination object is determined. Subsequently the first image data is modified using the determined delimitation and projection data is calculated from the modified first image data. The measurement data is modified using the projection data and finally second image data is reconstructed from the modified measurement data.

SUMMARY

At least one embodiment of the invention is directed to improving the reconstruction of image data from incomplete projection data.

Features and advantages or alternate forms of embodiment mentioned here are likewise also to be transferred to the other claimed objects and vice versa, in other words the object claims, which are directed to a system for example, can also be further developed with the features which are described or claimed in conjunction with a method. The corresponding functional features of the method are embodied in such cases by corresponding physical modules.

At least one embodiment of the inventive method is based on first projection data which is recorded during a relative rotational movement between an x-ray source of a CT device and at least one examination object lying partly outside the scanning area of the CT device. The first projection data thus involves incomplete projection data. The inventors have recognized that contour data of the surface of the examination object which was recorded by way of a camera can be used to improve the reconstruction of the incomplete first projection data. In this case the spatial correlation between the first projection data and the contour data is known.

At least one embodiment of the invention can further be realized in the form of an imaging system, which comprises a CT device with a rotatable x-ray source and also with an x-ray detector interacting with said x-ray source, and wherein the CT device is designed for recording first projection data of an examination object within or outside the scanning area of the CT device. At least one embodiment of the inventive imaging system further comprises a camera, designed for recording contour data of the surface of the examination object, wherein the spatial correlation between the first projection data and the contour data is known, and also a processing unit designed to expand the first projection data to modified projection data by means of the contour data. In addition, at least one embodiment of the inventive imaging system comprises a reconstruction unit, designed for reconstruction of image data by way of the modified projection data. With such an inventive system, at least one embodiment of the inventive method is able to be carried out advantageously in the described variants.

BRIEF DESCRIPTION OF THE DRAWINGS

The invention will be described and explained in greater detail below with reference to the example embodiments presented in the figures.

In the figures.

DETAILED DESCRIPTION OF THE EXAMPLE EMBODIMENTS

Figure 1:
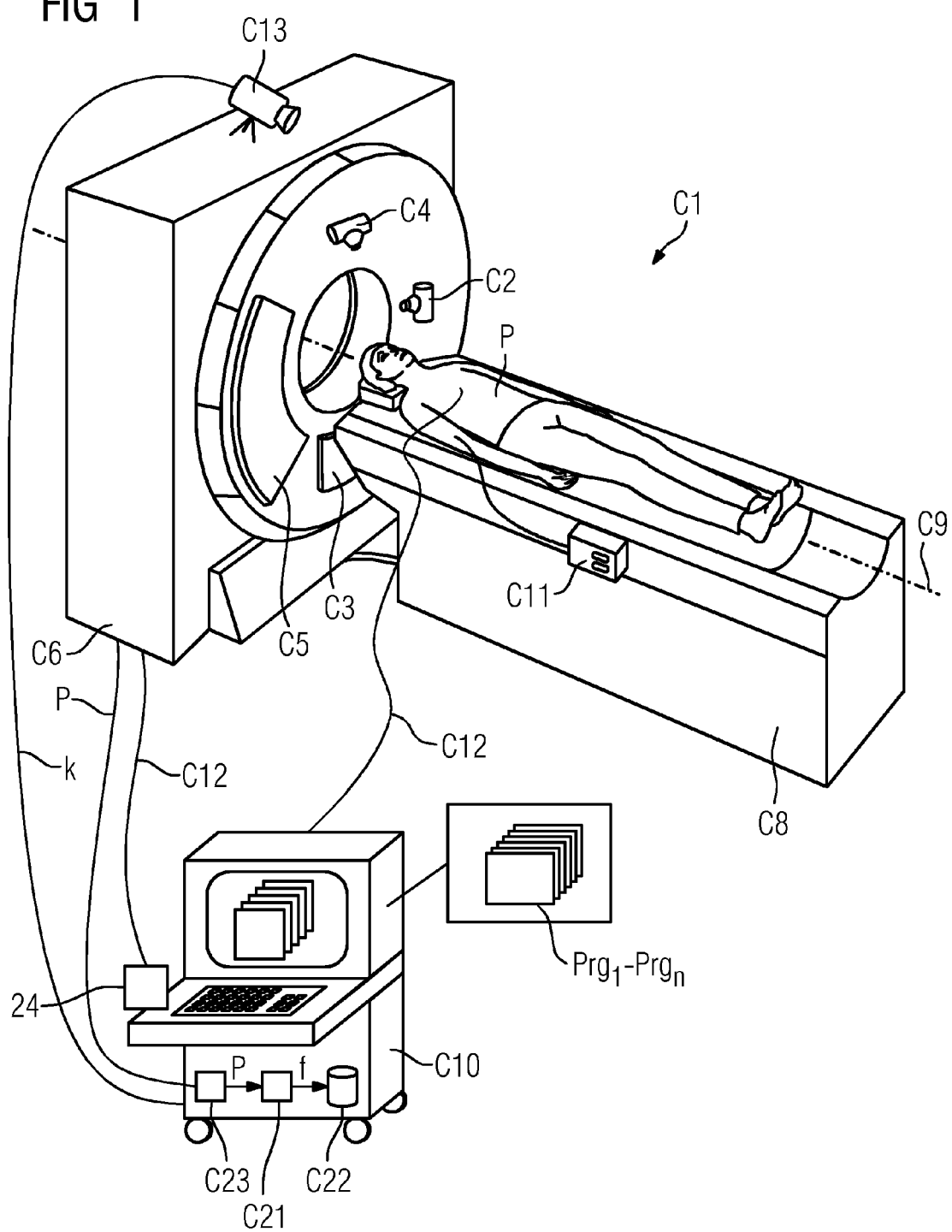
FIG. 1: shows a first schematic diagram of an example embodiment of an imaging system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the inventive method is based on first projection data which is recorded during a relative rotational movement between an x-ray source of a CT device and at least one examination object lying partly outside the scanning area of the CT device. The first projection data thus involves incomplete projection data. The inventors have recognized that contour data of the surface of the examination object which was recorded by way of a camera can be used to improve the reconstruction of the incomplete first projection data. In this case the spatial correlation between the first projection data and the contour data is known.

In accordance with at least one embodiment of the invention the first projection data is expanded by way of the contour data to modified projection data, so that the modified projection data includes information about the contour of the examination object lying outside the scanning area of the CT device. By contrast with conventional methods, the projection data is expanded by means of contour data which has been recorded by a camera. Such contour data recorded by means of a camera has an especially high information content which allows the incomplete first projection data to be expanded especially well. Thus fewer or no artifacts occur during the inventive reconstruction of image data by means of the modified projection data by comparison with reconstruction of image data from just the first image data.

In accordance with a further aspect of at least one embodiment of the invention first image data is reconstructed from the incomplete, first projection data, in order to then modify the first image data by means of the contour data. Furthermore modified projection data is created from the modified image data, so that second image data can be reconstructed from the first projection data and also from the modified projection data. In this aspect the information content of the contour data is taken into account during a modification in the image space, wherein such a modification is able to be achieved especially intuitively for a user of an inventive imaging system. Thus the first image data and the contour data can be represented graphically on an output unit. Furthermore at least one embodiment of the inventive method in accordance with this aspect can be carried out iteratively, by which the reconstruction of the image data by the additional iteration steps delivers better results, i.e. results that are prone to artifacts to a lesser extent.

In accordance with a further aspect of at least one embodiment of the invention the first image data is modified such that, by means of a correlation between the first image data and the contour data, a boundary surface of the examination object is defined in the first image data. Such a definition of the boundary surface represents a significant expansion of incomplete projection data and therefore, in a subsequent reconstruction, to a large extent rectifies artifacts which result from the incompleteness of the projection data.

In accordance with a further aspect of at least one embodiment of the invention the boundary surface involves the surface of the examination object, wherein the first image data is modified such that pixel values will be modified in an area outside the scanning area and within the area delimited by the surface, as the incompleteness of projection data is typically based on incomplete information in the vicinity of the surface of an examination object. Artifacts which are the result of incomplete information in the vicinity of the surface can be reduced or avoided if the additional information about the surface is taken into account by the pixel values in the area of the examination object not completely scanned being modified, which is done in accordance with at least one embodiment of the invention by way of the contour data.

In accordance with a further aspect of at least one embodiment of the invention the examination object involves a patient, whereby at least one anatomical landmark is identified in the contour data, wherein the pixel values in the area of the landmark will be modified as a function of a typical x-ray absorption of these landmarks. The landmark can especially involve a region of the patient's body, i.e. the head, the eyes, the thorax, the chest, the legs or an individual knee joint for example. Different landmarks exhibit a different x-ray absorption, for example, because they primarily consist of different materials such as bone, fat or water. Since a specific x-ray absorption correlates with specific values in reconstructed image data, this aspect of at least one embodiment of the invention offers an especially precise option for expanding incomplete projection data.

In accordance with a further aspect of at least one embodiment of the invention a sinogram is determined from the first projection data, wherein the first projection data will be expanded to modified projection data by an extrapolation of the sinogram. In this case no reconstruction has to take place before the expansion of the projection data, which means that at least one embodiment of the inventive method can be carried out with less computing effort and thus especially quickly.

In accordance with a further aspect of at least one embodiment of the invention the first projection data is expanded such that this first projection data is weighted in accordance with the correlated contour data. In such cases in particular individual rays within individual projections can be weighted. An inventive weighting makes provision for example for complete projections or rays to be given a greater weight than incomplete projections or rays. A method in accordance with this aspect of at least one embodiment of the invention can especially be combined with an iterative reconstruction algorithm. The projection data is then further expanded with each iteration step so that the resulting reconstruction of image data exhibits artifacts to a lesser extent and will thus be improved.

In accordance with a further aspect of at least one embodiment of the invention, the first examination object involves a patient, wherein a second examination object is identified by means of the contour data, wherein, depending on the identity and position of the second examination object, information is output at an output unit connected to a CT device. This makes it possible to take account during the reconstruction of further examination objects which lie partly or even entirely outside the scanning area and thus provide the user of an inventive CT device with additional information.

In accordance with a further aspect of at least one embodiment of the invention, the second examination object involves a medical device for intervention, wherein the output of a graphical representation comprises at least a part of the two examination objects as well as the specification about the relative position of the examination objects in relation to one another. At least one embodiment of the invention can thus be used to design an intervention, by means of a needle or an endoscope for example, more precisely and reliably.

In accordance with a further aspect of at least one embodiment of the invention the output involves a warning, by which safety during the continuing recording of projection data and also during interventions will be enhanced.

In accordance with a further aspect of at least one embodiment, the camera involves a 3D camera and the contour data involves 3D contour data, making the information content of the contour data especially high and thus making possible an especially precise expansion of the projection data and thus a reconstruction of image data that is prone to artifacts to an especially small extent. Furthermore, as a result of the high information content of the contour data, a result can be achieved during an iterative reconstruction especially quickly.

At least one embodiment of the invention can further be realized in the form of an imaging system, which comprises a CT device with a rotatable x-ray source and also with an x-ray detector interacting with said x-ray source, and wherein the CT device is designed for recording first projection data of an examination object within or outside the scanning area of the CT device. At least one embodiment of the inventive imaging system further comprises a camera, designed for recording contour data of the surface of the examination object, wherein the spatial correlation between the first projection data and the contour data is known, and also a processing unit designed to expand the first projection data to modified projection data by means of the contour data. In addition, at least one embodiment of the inventive imaging system comprises a reconstruction unit, designed for reconstruction of image data by way of the modified projection data. With such an inventive system, at least one embodiment of the inventive method is able to be carried out advantageously in the described variants.

FIG. 1 initially shows a schematic diagram of a first imaging system with a CT device. This involves a so-called third-generation CT device, to which embodiments of the invention are not restricted however. Located in the gantry housing C6 is a closed gantry not visible here, on which a first x-ray source C2 in the form of an x-ray tube with an x-ray detector C3 opposite said source are disposed. Optionally a second x-ray tube C4 with an opposing x-ray detector C5 is disposed in the CT device C1 shown here, so that a greater temporal resolution can be achieved through the additional emitter/detector combination available, or when different x-ray energy spectra are used in the emitter/detector systems, so-called "dual-energy" examinations can also be carried out.

The CT device C1 also has a patient couch C8, on which a patient can be pushed along a system axis C9, also referred to as the z-axis during the examination into the scanning area or into the FOV (abbreviation for "field of view"). It is however also possible for the scanning itself to be undertaken as a pure orbital scanning without any advance of the patient exclusively in the examination region of interest. The movement of the patient couch C8 relative to the gantry is effected by a suitable motorization. During this movement the x-ray source C2 or C4 each rotate around the patient. In this case the detector C3 or C5 runs in parallel opposite the x-ray source C2 or C4, in order to record first projection data p, which will then be used for reconstruction of image data, for example of slice images. As an alternative to a sequential scan, in which the patient is pushed in stages between the individual scans through the examination field, the option of a spiral scan is naturally also provided, in which the patient is pushed during the orbiting scan with the x-ray radiation continuously along the system axis C9 through the examination field between x-ray tubes C2 or C4 and detectors C3 or C5. Through the movement of the patient along the axis C9 and the simultaneous orbit of the x-ray source C2 or C4 a helical track is produced during a spiral scan for the x-ray source C2 or C4 relative to the patient during the measurement. This track can also be achieved by the gantry being pushed along the axis C9 with immobile patients. It is further possible to move the patient continuously and possibly periodically back and forth between two points.

The CT system C1 is controlled by a control and processing unit C10 with computer code Prg1 to Prgn present in a memory. It is pointed out that these computer program codes Prg1 to Prgn can of course also be contained on an external storage medium and can be loaded if required into the control and processing unit C10.

Acquisition control signals AS can be transmitted by the control and processing unit C10 via a control interface 24 to control the CT device in accordance with specific measurement protocols. The acquisition control signals AS here relate to the x-ray tubes C2 and C4, wherein specifications can be made relating to their power and the times at which they are switched on and switched off, as well as the gantry, wherein specifications can be made relating to its speed of rotation as well as the couch advance.

Since the control and processing unit C10 has an input console, measurement parameters can be entered by a user or an operator of the CT device C1 which then control the data acquisition in the form of acquisition control signals. Information about measurement parameters currently being used can be presented on the output unit in the form of the screen; in addition further information relevant for the operator can be displayed. The inventive imaging system can also include further output units, such as an acoustic output unit for example.

The first projection data p or raw data recorded by the detectors C3 or C5 is transferred via a raw data interface C23 to the control and processing unit C10. This first projection data p is then, if necessary after suitable pre-processing, further processed in a reconstruction unit C21. The reconstruction unit C21 in this exemplary embodiment is realized in the control and processing unit C10 in the form of software on a processor, e.g. in the form of one or more of the computer program codes $Prg_1$ to $Prg_n$. In relation to the image reconstruction what has already been explained in relation to the control of the measurement process applies, i.e. that the computer program codes $Prg_1$ to $Prg_n$ can also be contained on an external storage medium and can be loaded into the control and processing unit C10 if required. It is further possible for the control of the measurement process on the one hand and the image reconstruction on the other hand to be carried out by different processing units.

The image data f reconstructed by the reconstruction unit C21 is then stored in a memory C22 of the control and processing unit C10 and/or output in the usual manner on the screen of the control and processing unit C10. It can also be fed via an interface not shown in FIG. 1 into a network connected to the CT device C1, for example a radiological information system (RIS), and stored in mass storage available there or output as images.

The control and processing unit C10 can additionally perform the function of an EKG, wherein a line C12 for deriving the EKG potentials is used between patient and control and processing unit C10. In addition the CT system C1 shown in FIG. 1 also has a contrast medium injector C11, via which additional contrast medium can be injected into the bloodstream of the patient, so that e.g. the blood vessels of the patient, especially the heart chambers of the beating heart, can be better represented. In addition this also provides the option of carrying out perfusion measurements for which the proposed method is likewise suitable.

The control and processing unit C10—unlike the diagram depicted in FIG. 1—of course does not have to be located in the vicinity of the remaining components of the CT system C1. Instead it is possible to accommodate said unit in another room or in a location further away. The raw data p and/or the acquisition signals AS and/or the EKG data can be transmitted over a wire or alternately wirelessly.

An embodiment of the inventive imaging system also has at least one camera C13 which is designed for non-contact scanning of at least a part of the surface of the examination object O. The camera C13 is designed for detection of electromagnetic radiation, especially for detection of electromagnetic radiation in a lower frequency range of the spectrum creation by comparison with x-ray radiation, for example in the visible or infrared range of the spectrum. Thus the camera C13 can involve one or more photographic camera(s) or video camera(s). In the example shown here the camera C13 involves a 3D camera attached to the gantry, which is embodied for example as a stereo camera or as a runtime measurement system (known as a time-of-flight camera). In a further embodiment of the invention the camera C13 is embodied to scan a surface by means of structured illumination. In this embodiment the imaging system additionally has an illumination unit generating a structured illumination of at least one part of the examination object O. Furthermore in this case the camera C13 and the illumination unit are positioned and embodied in their emission and detection characteristics so that the camera C13 is embodied for detection of the radiation reflect from the surface of the examination object O.

In a further form of embodiment of the invention, the electromagnetic sensor 31 is integrated permanently into the gantry of the CT device C1. In an alternate form of embodiment the camera C13 is integrated into the rotatable part of the gantry 19 such that the camera C13 rotates with the x-ray source C2 or with the x-ray detector C3 respectively. This enables the surface of the examination object O to be scanned especially easily and quickly from different perspectives. The additional surface information enables the contour data k of the scanned surface to be computed especially precisely so that the inventive method can also be executed especially easily, quickly and precisely. To carry out the inventive method the coordinates of the recorded contour data k must be able to be converted into the coordinates of the projection data. Then the contour data k can also be converted into the image space of the image data f. In other words the correlation of the contour data k and also the projection data, especially the first projection data p must be known. Such a correlation is able to be determined by a calibration which precedes the inventive method.

Figure 2:
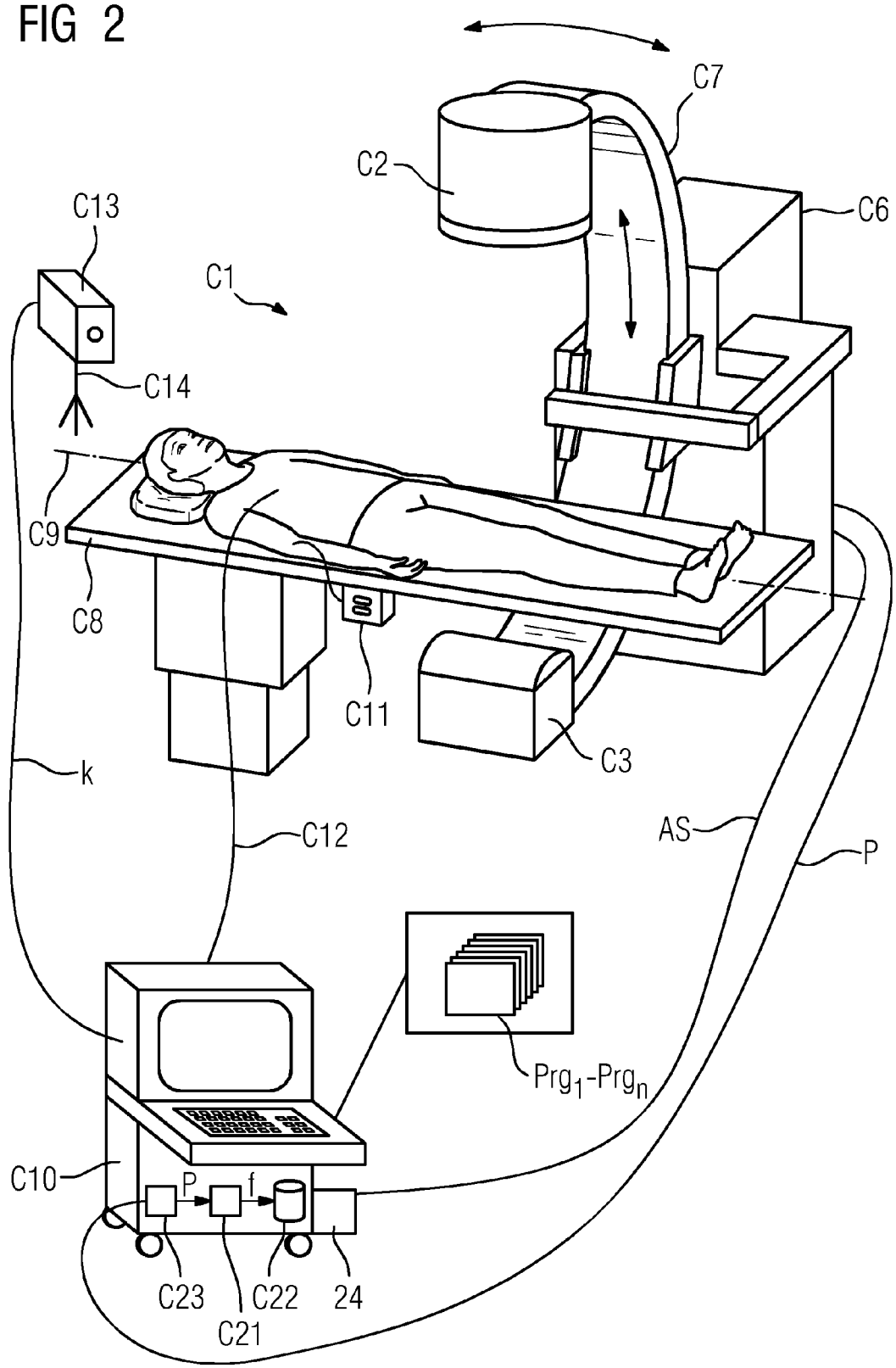
FIG. 2: shows a second schematic diagram of an example embodiment of an imaging system.

FIG. 2 shows an imaging system with a C-arm device, in which, by contrast with the CT device of FIG. 1, the housing C6 bears the C-arm C7, to one side of which the x-ray tube C2 is fastened and to the opposing side of which the x-ray detector C3 is fastened. The C-arm C7 is likewise pivoted around a system axis C9 for a scan, so that a scan can take place from a plurality of scanning angles and corresponding first projection data p can be determined from a plurality of projection angles. The C-arm system C1 of FIG. 2, like the CT system from FIG. 1, also has a control and processing unit C10 of the type described for FIG. 1.

With the form of embodiment of the invention shown in FIG. 2, the camera C13 is mounted on a positioning facility in the form of a tripod C14. Furthermore the camera C13 can also be positioned in some other way in the space in which the CT device C1 is located, for example the camera C13 can be fastened to the ceiling. Furthermore the camera C13 can be positioned centrally over the examination object O or centrally over the patient couch C8. If the camera C13 involves a 3D camera, then the contour data k also contains depth information about the detailed structure of the surface of the examination area. Basically it is advantageous for the camera C13 to be positioned so that the quality of the depth information about the scanned surface of the examination object O and thus also the quality of the recorded contour data k is as homogeneous as possible. The noise or the errors of depth information or of the contour data k determined by scanning should depend to smallest extent possible on the depth information or the contour data k itself or on the position of the scanned area.

Embodiments of the invention is able to be used in both of the systems shown in FIGS. 1 and 2. Furthermore it is basically also able to be used for other CT devices, e.g. for CT devices with a detector forming a complete ring.

For image reconstruction the presence of a complete dataset of projection data is advantageous. Complete in this context means that each volume element of the examination object O, which is to be included in the reconstructed image, must be irradiated over a range of projection angles of 180°, if measurement is being undertaken in parallel ray geometry, or of 180° plus the cone opening angle, if measurement is being undertaken in cone beam geometry, and the corresponding projections must be detected by the x-ray detector. If these conditions are not met then image reconstruction is still possible, however the resulting image is prone to artifacts because of the incompleteness of the dataset of the projection data.

Figure 3:
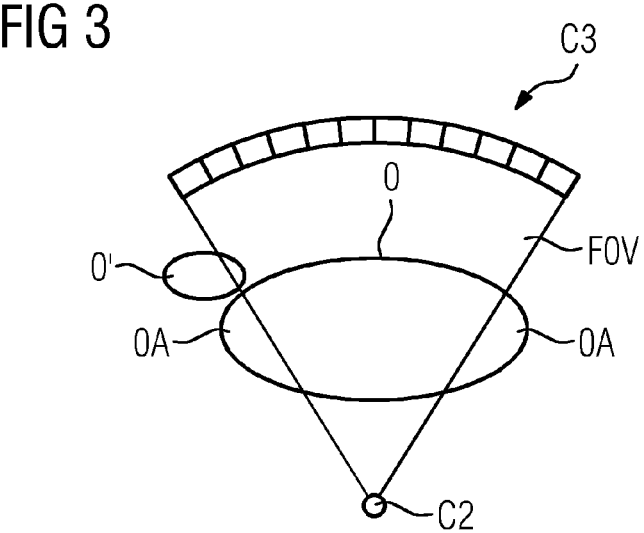
FIG. 3: shows a section of the recording geometry perpendicular to the z-direction.

Problems arise if the extent of the examination object O is greater than the field of view FOV of the CT device C1. Such a situation is shown in FIG. 3. This figure shows a section from a CT device in accordance with FIG. 1 or 2, which comprises the x-ray source C2 and the x-ray detector. For enhanced clarity the x-ray detector C3 only has 12 detector elements in the channel direction; in reality the number is far greater. The examination object O is located between the x-ray source C2 and the x-ray detector C3. FIG. 3 shows a section perpendicular to the z-axis; thus an axial section through the examination object O is to be seen. The field of view FOV of the CT device C1 corresponds at a specific projection angle, as shown in FIG. 3, in a cross-section perpendicular to the z-axis, to a circular section. Its edges are formed by the x-rays which arrive at the outermost edges of the detector C3 from the x-ray source C2.

It is thus the extent of the detector in the channel direction that determines the size of the field of view FOV. The channel direction here is the direction onto the surface of the detector perpendicular to the row direction. The row direction extends at right angles to the plane of the section of FIG. 3 and thus in the z-direction. The detector dimension in the drawing plane of FIG. 3 is the channel direction.

It can be seen in FIG. 3 that the examination object 5, for the projection angle shown, does not lie completely within the field of view FOV. The elements OA of the examination object O, for the position of x-ray source C2 and x-ray detector C3 in accordance with FIG. 3 are not illuminated by x-rays which are detected by the x-ray detector C3: The elements OA of the examination object O lie outside the field of view FOV. If x-ray source C2 and detector C3 are rotating around the examination object O, then, in the arrangement depicted in FIG. 3, for some projection angles the parts OA of the examination object O lying outside the field of view FOV lie within the field of view FOV, for other projection angles they lie outside the field of view FOV. The same also applies for the other edge areas of the examination object O.

This means that complete projection data is not present for some elements of the examination object O. In general it is true to say that the entire field of view of the CT device C1, i.e. that area between x-ray source C2 and x-ray detector C3 for which complete projection data is recorded, is produced by the number of intersections of the beams over a half orbit of x-ray source C2 and x-ray detector C3—or over a half orbit of 180° plus the cone opening angle. The extended field of view of the CT device C1 is an area which is adjacent to the described area of the overall field of view. The extended field of view, which includes those volume elements which are only irradiated by x-ray radiation which subsequently reaches the detector at some projection angles, lies outside the overall field of view.

For elements of the examination object O within the extended field of view, such as the part OA of FIG. 3 for example, this means that, in some of the recorded projections, information relating to these parts of the examination object O is contained in the measurement data, but in other projections it is not. In relation to the elements of the examination object O which are located in the extended field of view an incomplete dataset is thus available. This is also referred to as "limited angle" scanning.

Parts of an examination object O exceeding the field of view occurs in practice for example as a result of the body volume of the patients, or because the patient during a thorax measurement is not in a position to place their arms above or behind their head.

Since information relating to the examination object O is contained within the expanded field of view in some projections, it is not easily possible to reconstruct a CT image only for the area of the overall field of view. Instead exceeding the field of view leads to the CT image being prone to artifacts within the overall field of view. The reason for this is the incompleteness of the data of the extended field of view explained above. The information of the extended field of view must therefore be taken into account during image reconstruction.

Figure 4:
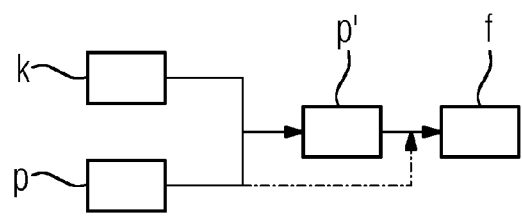
FIG. 4: shows a flow diagram of a variant of an embodiment of the inventive method.

A flow diagram of a variant of the inventive method is shown in FIG. 4. An embodiment of the inventive method is based on first projection data p which has been recorded during a relative rotational movement between an x-ray source C2 of a CT device C1 and at least one examination object O lying partly outside the field of view FOV of the CT device C1. At least parts of the first projection data are thus incomplete and require reconstruction in the expanded field of view in order to avoid artifacts. For such a reconstruction contour data k of the surface of the examination object O has been recorded by means of a camera C13. The contour data k involves data which includes information about the contour of the examination object O, especially outside the field of view FOV. In an advantageous way the contour data k has been recorded by means of a 3D camera, so that the contour data includes more detailed depth information about the contour of the examination object. The contour data k can also involve pre-processed, i.e. filtered or reconstructed data. It is thus possible to define a boundary surface of the examination object O in the contour data k recorded by the camera, for example by means of an edge detection algorithm. In such cases the spatial correlation between the first projection data p and the contour data k is known. The coordinates of the contour data k can thus be converted into the coordinates of the projection data p. Therefore in accordance with the invention the contour data k can be used to expand the first, incomplete projection data p to modified projection data p'. The subsequent reconstruction of image data f by way of the modified projection data p' exhibits artifacts to a lesser extent as a result of the expansion of the first projection data than would be the case for a comparable reconstruction of the original first projection data p.

The reconstruction can be undertaken with conventional methods, i.e. with filtered back projection, a cone beam reconstruction and also with an iterative or algebraic method for example. The first projection data p is typically expanded by an extrapolation. In this case above all the incomplete projections are expanded, but it can also be technically advantageous to expand complete projections, for example to guarantee certain continuities between different projections. In a further embodiment of the invention the rays of an individual projection are weighted, through which even more information, based on the contour data k, is taken into account, so the reconstruction leads to better image data f i.e. image data prone to artifacts to a lesser extent. Furthermore the original first projection data p can also be taken into account as well in the reconstruction, by the first projection data p and the modified projection data p' being mixed for example.

In a further form of embodiment of the invention a sinogram is determined from the first projection data p, wherein the first projection data p can be expanded by extrapolation of the sinogram to modified projection data p'. The sinogram can involve a 2D as well as a 3D sinogram, wherein a 3D sinogram is typically embodied as a stack of a plurality of 2D sinograms. The extrapolation can in such cases especially be undertaken along the individual rows and columns of a 2D sinogram. A sinogram expanded by extrapolation contains additional information in the extended field of view, so that modified projection data p' derived from the expanded sinogram likewise has additional information in the extended field of view. The extrapolation is undertaken for example by means of polynomial or trigonometric functions. In accordance with the invention the extrapolation is undertaken by means of the contour data k, i.e. taking into account the information about the contour of the examination object O. Since the contour data k has been recorded via a camera and therefore provides precise information about the contour of the examination area O, the invention makes it possible to extrapolate sinograms especially precisely and efficiently, so that a corresponding reconstruction in the extended field of view rapidly leads to especially good results in the form of image data f.

Figure 5:
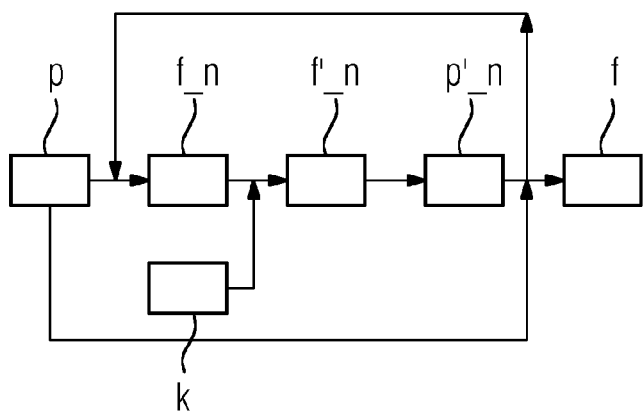
FIG. 5: shows a flow diagram of a further variant of an embodiment of the inventive method.

A flow diagram of a further variant of an embodiment of the invention is shown in FIG. 5. Since the method in accordance with the variant shown here can also be executed iteratively, the index n specifies the respective iteration cycle below. Thus, in a first iteration, first image data f_1 is reconstructed from the first projection data p. Then the first image data f_1 is modified by way of the contour data k. The expansion thus takes place in the image space. If modified projection data p'_1 is generated from the modified image data f', then the modified projection data p'_1 especially in the extended field of view has an increased information content compared to the first projection data p. Therefore second image data f_2 can be reconstructed especially advantageously from the first projection data p and also from the modified projection data p'. The specified iteration cycle is able to be repeated until such time as an abort criterion is reached. The abort criterion is given for example by an absolute number of maximum iterations or by falling below a predetermined difference of the image information between two items of reconstructed image data f_n and f_n+1.

The expansion in the image space can be utilized advantageously in different forms of embodiment of the invention. In one form of embodiment of the invention the image data f_n is modified such that, by means of a correlation between the first image data and the contour data, a boundary surface of the examination object O is defined in the image data f_n. The boundary surface can especially involve a surface of the examination area O. The defining of a boundary surface in the image data allows the pixels on the two sides of the boundary surface to be processed differently and thereby additional information to be provided. In a form of embodiment of the invention the image data f_n is modified such that pixel values in an area outside the field of view FOV and within the area delimited by the surface will be modified. Thus the respective pixel values can assume quite specific attenuation values which are to be expected as a result of the contour data k or the information derived from it such as the boundary surface.

If the examination object involves a patient, in a further form of embodiment of the invention, at least one anatomical landmark is identified in the contour data, so that the pixel values in the area of the landmark will be modified as a function of a typical x-ray absorption of this landmark. If the landmark involves an arm, the corresponding pixel values can be modified so that they correspond to the x-ray absorption which is produced by a mixture of materials such as bones and muscle tissue typical for an arm.

In a further embodiment of the invention a second examination object O' is identified by means of the contour data k, wherein, as a function of the identity and position of the second examination object O', an output is made to an output unit connected to the CT device C1. Thus a warning can be output if a second examination object, for example in the form of a C-arm or a hose, is located too close to the patient. In a further form of embodiment of the invention the second examination object O' involves a medical device for intervention, wherein the output comprises a graphical representation of at least a part of the two examination objects O as well as the specification about the relative position of the examination objects in relation to one another. This enables the inventive method to also be used for navigation during surgical interventions.

In further forms of embodiment of the invention, the recording of the first projection data p and also the recording of the contour data k and further steps described here as preceding embodiments of the inventive method, can be themselves embodied as part of the inventive method.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in detail on the basis of the preferred exemplary embodiment, the invention is not limited by the disclosed examples and other variations can be derived herefrom by the person skilled in the art, without departing from the scope of protection of the invention.

What is claimed is:

1. A method for reconstruction of image data, wherein first projection data has been recorded during relative rotational movement between an x-ray source of a computed tomography (CT) device and at least one examination object, wherein contour data of a surface of the at least one examination object has been recorded via a camera, wherein at least a portion of the at least one examination object is outside the field of view of the CT device, and wherein a spatial correlation between the first projection data and the contour data is known, the method comprising:
   expanding the first projection data by way of the contour data to generate modified projection data; and
   reconstructing the image data using the modified projection data.

2. The method of claim 1, wherein
   the expanding the first projection data includes
      reconstructing first image data from the first projection data,
      modifying the first image data by way of the contour data, and
      creating the modified projection data from the modified first image data; and
   the reconstructing reconstructs the image data from the first projection data and the modified projection data.

3. The method of claim 2, wherein the modifying the first image data comprises:
   modifying the first image data based on a correlation between the first image data and the contour data, to define a boundary surface of the at least one examination object in the first image data.

4. The method of claim 3, wherein
   the boundary surface includes the surface of the at least one examination object; and
   the modifying the first image data further includes modifying pixel values in an area outside the field of view and within an area delimited by the surface.

5. The method of claim 4, wherein
   the at least one examination object includes a patient;
   at least one anatomical landmark is identified in the contour data; and
   the pixel values in an area of the anatomical landmark are modified as a function of x-ray absorption of the anatomical landmark.

6. The method of claim 1, wherein the expanding the first projection data comprises:
   determining a sinogram from the first projection data; and
   extrapolating the sinogram to generate the modified projection data.

7. The method of claim 1, wherein the expanding the first projection data comprises:
   expanding the first projection data by weighting in accordance with the contour data.

8. The method of claim 1, wherein
   the at least one examination object includes a first examination and a second examination object;
   the first examination object includes a patient; and
   the method further includes
      identifying the second examination object by way of the contour data, and
      generating an output as a function of the identity and position of the second examination object.

9. The method of claim 8, wherein
   the second examination object includes a medical device for intervention; and
   the output includes a graphical representation of at least one part of the first and second examination objects and a specification of the position of the first and second examination objects relative to one another.

10. The method of claim 8, wherein the output includes a warning message.

11. The method of claim 1, wherein the camera is a 3D camera and the contour data includes 3D contour data.

12. The method of claim 2, wherein the camera is a 3D camera and the contour data includes 3D contour data.

13. The method of claim 8, wherein the camera is a 3D camera and the contour data includes 3D contour data.

14. The method of claim 9, wherein the camera is a 3D camera and the contour data includes 3D contour data.

15. An imaging system, comprising:
   a computed tomography (CT), device, including a rotatable x-ray source and an x-ray detector, the CT device configured to record first projection data of at least one examination object, at least a portion of the at least one examination object being outside the field of view of the CT device;
   a camera configured to record contour data of a surface of the at least one examination object, wherein a spatial correlation between the first projection data and the contour data is known; and at least one processor configured to execute computer readable instructions to
expand the first projection data by use of the contour data to generate modified projection data, and
reconstruct image data using the modified projection data.

16. The imaging system of claim 15, wherein
the at least one examination object includes a first examination object and a second examination object;
the first examination object includes a patient;
the second examination object is identified by way of the contour data; and
the imaging system further includes an output unit connected to the CT device, the output unit configured to provide an output as a function of the identity and position of the second examination object.

17. The imaging system of claim 15, wherein the camera is a 3D camera and the contour data includes 3D contour data.

18. The imaging system of claim 16, wherein the camera is a 3D camera and the contour data includes 3D contour data.

19. The method of claim 9, wherein the output includes a warning message.

20. The method of claim 19, wherein the camera is a 3D camera and the contour data includes 3D contour data.

* * * * *